United States Patent
Peeters

(10) Patent No.: US 7,492,864 B2
(45) Date of Patent: Feb. 17, 2009

(54) METHODS AND APPARATUS FOR RANGE BASED X-RAY ATTENUATION

(75) Inventor: David Peeters, Bloomingdale, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/832,204

(22) Filed: Aug. 1, 2007

(65) Prior Publication Data
US 2008/0170657 A1    Jul. 17, 2008

Related U.S. Application Data

(60) Provisional application No. 60/885,018, filed on Jan. 16, 2007.

(51) Int. Cl.
H05G 1/10    (2006.01)
(52) U.S. Cl. .................. 378/95; 378/162; 378/165
(58) Field of Classification Search .................. 378/64, 378/65, 91, 95, 96, 98, 101, 114–117, 207, 378/162, 165
See application file for complete search history.

(56) References Cited

U.S. PATENT DOCUMENTS

| 5,270,925 | A  | * | 12/1993 | Stegehuis | 378/7 |
| 6,369,401 | B1 | * | 4/2002  | Lee | 250/559.21 |
| 6,662,036 | B2 |   | 12/2003 | Cosman | |
| 7,199,382 | B2 |   | 4/2007  | Rigney et al. | |
| 2004/0131145 | A1 | * | 7/2004 | Ohara | 378/37 |
| 2006/0066453 | A1 |   | 3/2006 | Homanfar et al. | |

* cited by examiner

*Primary Examiner*—Jurie Yun
(74) *Attorney, Agent, or Firm*—Alexander J. Burke; Peter L. Kendall

(57) ABSTRACT

Methods and apparatus are disclosed for automatically setting an X-Ray strength based at least in part on the volume of an object. Lasers are used to measure distances to the object. Using the measured distances, a volume of the object to be X-Rayed is estimated. Using the estimated volume, an appropriate X-Ray strength is determined and an X-Ray machine is adjusted to provide X-Rays of that strength.

21 Claims, 4 Drawing Sheets

METHODS AND APPARATUS FOR RANGE BASED X-RAY ATTENUATION

This application claims the benefit of U.S. Provisional Application No. 60/885,018, filed Jan. 16, 2007, which is incorporated herein by reference.

FIELD

The present invention relates generally to X-Ray machines and more particularly to range based X-Ray attenuation.

BACKGROUND

X-Ray technology has been employed extensively in medical imaging and other imaging fields. Objects (e.g., patients) of a greater volume require stronger X-Rays (e.g., X-Ray beams with higher energy and/or power applied) to pass all the way through the object. Failure to adjust for the volume of the object being X-Rayed results in substandard imagery. If the X-Ray beams carry too much energy, the patient appears too transparent; if the X-Ray beams carry too little energy, the patient appears too obscured (e.g., dark).

However, in current medical X-Ray machines adjusting the strength of the X-Ray requires a time-consuming editing of advanced settings of the X-Ray machine.

SUMMARY

An embodiment of the present invention provides an improved technique for automatically setting X-Ray strength. In one embodiment, the volume of an object to be X-Rayed is estimated and an X-Ray strength is automatically selected based on the estimated volume. In one embodiment, the volume may be estimated to be within one of a plurality of ranges (e.g., small, medium, large, etc.). An X-Ray machine is then configured to transmit X-Rays at the selected strength.

In one embodiment, the volume is estimated by using lasers or other collimated light beams to determine one or more distances to the to object to be X-Rayed and/or other objects such as support tables, etc.

These and other advantages will be apparent to those of ordinary skill in the art by reference to the following detailed description and the accompanying drawings.

DETAILED DESCRIPTION

Embodiments of the present invention generally provide methods and apparatus for automatically setting X-Ray strength. Specifically, an embodiment of the present invention estimates a volume of an object to be X-Rayed. Using the estimated volume, an appropriate X-Ray strength may be determined and an X-Ray machine may be adjusted to provide X-Rays of that strength.

Though discussed herein as X-Ray strength, it may be understood that this term may incorporate one or more parameters of X-Rays and/or X-Ray machines. Such parameters may include wavelength, frequency, amplitude, power, energy, voltage, current, etc. Accordingly, one or more of these parameters may be used interchangeably with X-Ray strength as each is contributory to "X-Ray strength."

Figure 1:
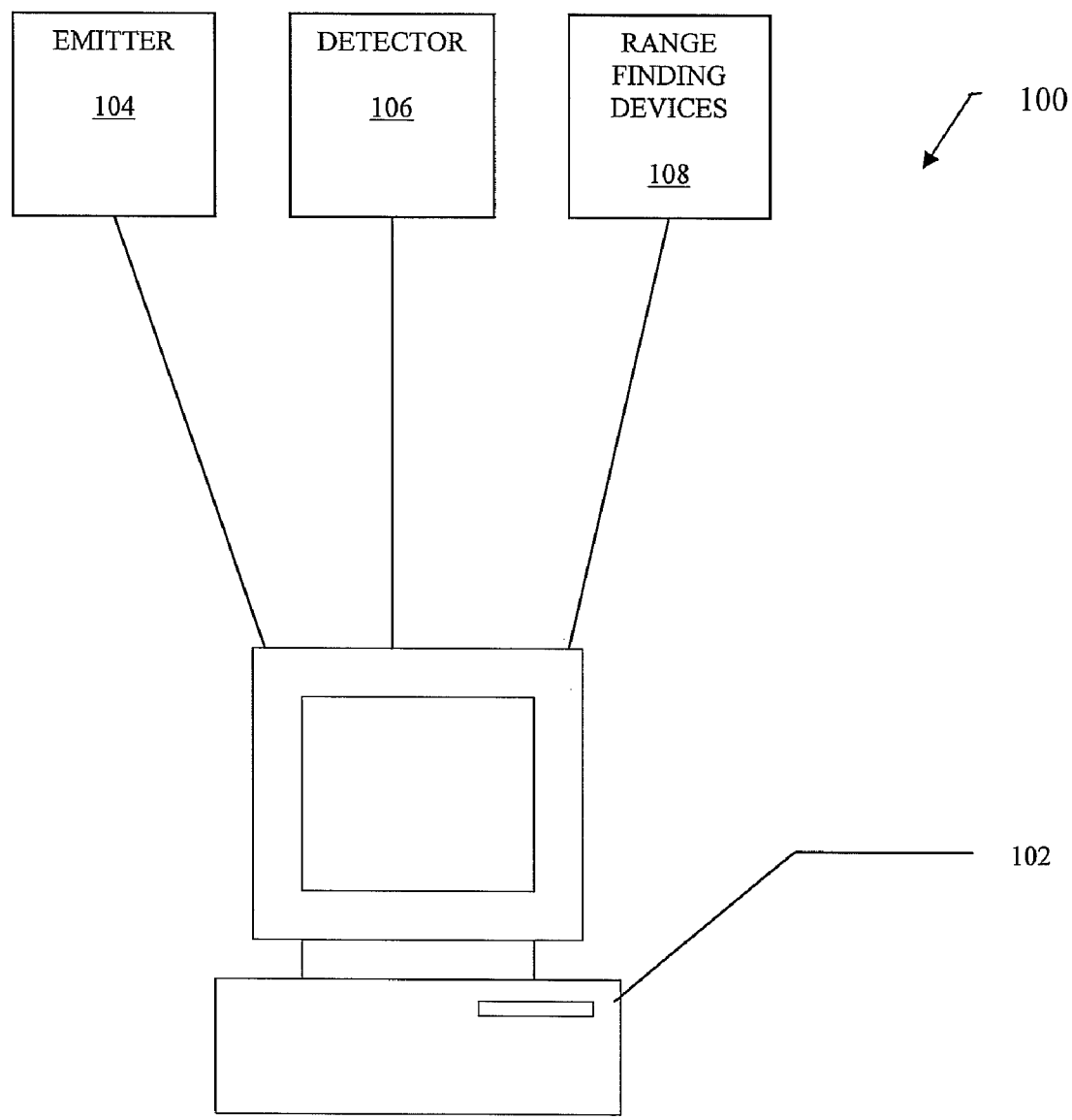
FIG. 1 is a schematic diagram of an X-Ray system in accordance with an embodiment of the present invention.

FIG. 1 is a schematic diagram of an X-Ray system 100. X-Ray system 100 may have a controller (e.g., computer) 102. Controller 102 may be coupled to an X-Ray emitter 104 and X-Ray detector 106. The controller 102 may further be coupled to one or more range finding devices 108.

X-Ray emitter 104 and X-Ray detector 106 may be of any type as is known in the art. X-Ray emitter 104 may be capable of emitting X-Rays at a predetermined and/or adjustable strength. That is, the wavelength and/or frequency of the X-Rays may be adjusted using various amounts of energy. X-Ray detector 106 may include a camera and/or film (not shown), silicon based charge coupled devices for use in digital X-Rays, and/or any other implements used in radiography.

Range finding devices 108 may be any device capable of determining a distance to an object. For example, range finding devices 108 may be lasers, ultrasonic distance meters, devices employing radar, or any other appropriate device.

Figure 2:
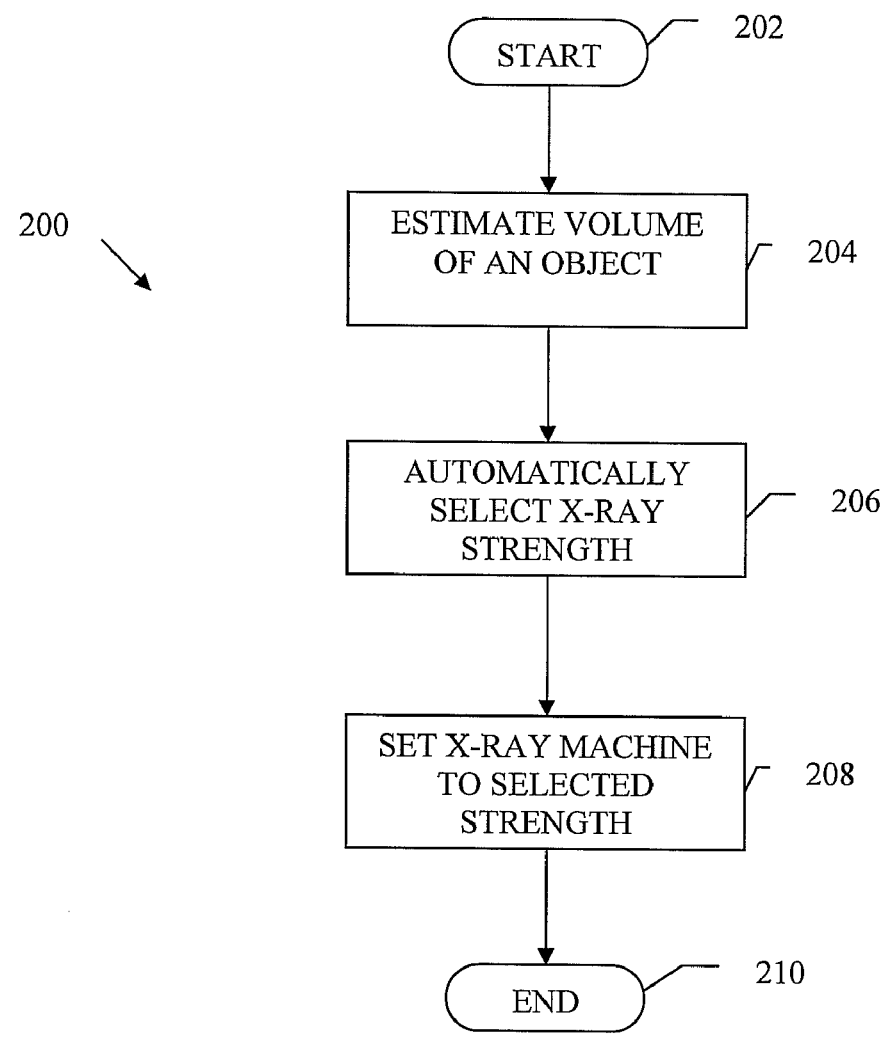
FIG. 2 shows a flowchart of a method for automatically setting X-Ray strength.

A method 200 for automatically setting X-Ray strength is depicted in FIG. 2. The method begins at step 202.

In step 204, a volume of an object is estimated. The volume may be automatically estimated. That is, the volume may be estimated by controller 102 using information from one or more measurement instruments such as range finding devices 108. This estimation may be made without input from a user subsequent to an initiation or start command. In at least one embodiment, the volume may be estimated with some input from a user and/or using information resident at memory 406 or another source.

In one embodiment, the volume is estimated by measuring a plurality of distances to a patient. These measurements may then be used to calculate an approximate volume of the patient. For example, one or more range finding devices 108 or sets (e.g., groups, clusters, etc.) of range finding devices 108 may measure (e.g., determine) distances to one or more surfaces of the patient. The range finding devices 108 may measure a distance to the first obstruction (e.g., a surface of the patient) and transmit this information to the controller 102. Based on the measured distances, a volume of the object may be estimated by one or more components of controller 102.

In the course of such estimation, certain parameters (e.g., dimensions such as width, length, etc.) of the patient may be set aside, projected, or estimated, such as by controller 102. For example, if a range finding device 108 measures a distance to a part of the patient (e.g., the top), another portion of the object (e.g., the bottom) may be assumed to be a predetermined distance away, such as lying on a surface (e.g., a table) at a known distance. Thus, the height of the patient (e.g., the distance from the top to the bottom) could be estimated by one or more components of controller 102 using the single measurement from the range finding device 108. An assumed and/or approximate width and/or length may be used to estimate the volume of the patient by one or more components of controller 102. In at least one embodiment, this width may itself be estimated based on height and a calculation of standard height to width proportions. In this way, a single distance measurement may be used to estimate the volume of the object.

In alternative embodiments, multiple range finding devices 108 or sets of range finding devices 108 may be used to measure distances. For example, a first range finding device (or set of range finding devices) may measure a first distance to a part of a patient (e.g., the top) and a second range finding device (or set of range finding devices) may measure a distance to another portion of the patient (e.g., the bottom). Alternatively, the second distance measurement may be made to a table of known size supporting the patient. Based at least in part on the measured distances and any known parameters (e.g., the table thickness) a volume of the patient may then be estimated by controller 102.

Controller 102 may employ one or more algorithms to estimate the volume of the object based at least in part on the measurement information received from the range finding devices 108. Such algorithms may round or otherwise approximate volumes into ranges. For example, the controller may estimate the volume of an object to be within one of three ranges—small, medium, or large. Any number of ranges and/or designations of such ranges (e.g., child, adult, obese) may be employed as appropriate. These ranges and/or X-Ray strengths could be displayed via an input/output device 112 for user information.

Additionally and/or alternatively in step 204, other parameters of the object or patient may be estimated. Such parameters may include density (e.g., the patients mass per unit volume), weight, mass, etc. These parameters may be measured and/or estimated as described herein (e.g., using measurements from range finding devices 118 to estimate weight, etc.) or may use other appropriate methods such as digital scales, etc. In this way, if any parameter can be measured or estimated, any other parameter which can be calculated therefrom may be used in addition to or in replacement of the estimated volume.

A particular embodiment using lasers as range finding devices 108 is described in more detail below with respect to FIG. 3. One of skill in the art would appreciate the methods which may be employed to use one or more measurements made by range finding devices 108 and/or other information to estimate the volume of an object.

In step 206, an X-Ray strength is automatically selected based on the estimated volume. The controller 102 may use the measurements received from the range finding devices 108 and/or the estimated volume calculated in step 204 to select the X-Ray strength. In this way, the controller may automatically choose an appropriate X-Ray strength based on the estimated volume without further input from a user.

In some embodiments, the controller 102 may select X-Ray strength based on a range. That is, for a certain subset of volumes, one strength is selected while a different strength is selected for another subset of volumes. These strengths may correlate to the ranges of volumes (e.g., small, medium, large, etc.) discussed above or may be determined based on an estimated volume that is not transmitted and/or used as a range or range designation. That is, the actual estimated volume may be transmitted and/or used to select the X-Ray strength, which is selected from a finite number of predetermined strengths. In the same or alternative embodiments, the X-Ray strength may be selected from a look-up table stored in memory 104 based on the estimated volume. Other methods of selecting the X-Ray strength may be used as appropriate.

In step 208, an X-Ray machine is set to the selected strength. Here, controller 102 may transmit control signals to emitter 104 indicative of the selected strength. Emitter 104 may then transmit X-Rays as directed by a user.

The method ends and step 210.

Figure 3:
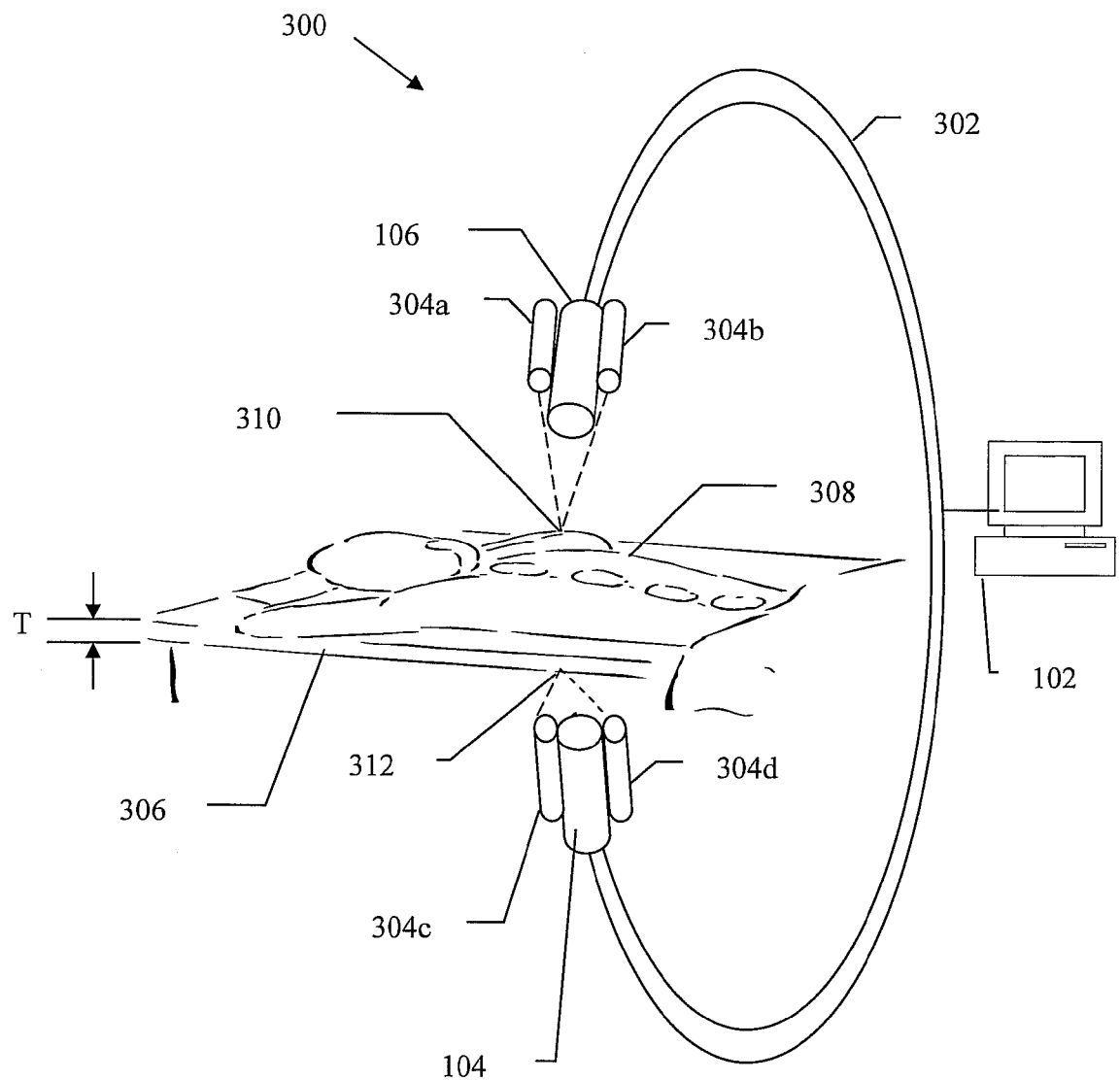
FIG. 3 is a diagram of an X-Ray machine according to a particular embodiment of the present invention.

FIG. 3 is a diagram of an X-Ray machine 300 according to a particular embodiment of the present invention. X-Ray machine 300 may incorporate similar structures as described above with respect to FIG. 1. Accordingly, such structures will not be described again in detail except for their interrelation in X-Ray machine 300.

X-Ray machine 300 has a support arm 302. Support arm 302 supports an emitter 104 and a detector 106. One or more lasers 304a-d may be coupled to the support arm 302, the emitter 104, and/or the detector 106. Coupled to one or more of support arm 302, emitter 104, detector 106, and/or lasers 304 may be a controller 102. Positioned between emitter 104 and detector 106 may be a support 306. Support 306 may be capable of supporting an object 308.

Support arm 302 may be a c-arm as is known and may be maneuverable and/or positionable in any number of directions to facilitate X-Ray functions. Other arms and/or supports may be used. For example, a multi-jointed arm as is common in dental X-Ray machines may be used. In such embodiments, the support arm 302 may support the emitter 104 and/or lasers 304, but not detector 106. In another exemplary embodiment, emitter 104 may be coupled to a track system for movement. In such embodiments, the lasers 304 may be coupled on or about the emitter 104 or may be located on another support. Other arrangements of the emitter 104, detector 106, and lasers 304 may be used as is convenient.

In one embodiment, the range finding devices 118 as described above with respect to FIG. 1 are lasers. The lasers 304 may be any device which uses a laser beam or other highly collimated beam of light in order to determine the distance to an object (e.g., a reflective object). Lasers 304 may operate on the time-of-flight principle by sending a laser pulse in a narrow beam towards the object and measuring the time taken by the pulse to be reflected off the first obstruction and returned to a detector. Other lasers, highly collimated beams of light, range finding devices, and/or measurement methods may be used.

Lasers 304 may be coupled to the emitter 104, the detector 106, the support arm 302, or any other structure. In the particular embodiment depicted in FIG. 3, lasers 304 may be supported proximal to a first and second end of the support arm 302, as shown. That is, the lasers 304 may be coupled and/or supported in the vicinity of emitter 104 and/or detector 106. Lasers 304 may be moveable and/or rotatable to facilitate distance measurements. Such lasers 304 may be controllable by the controller 102 and may communicate therewith, transmitting range information. Though shown in FIG. 3 as four lasers 304a-d, any number of lasers may be used.

Support 306 may be a table or other means of supporting an object (e.g., a body or patient in medical applications) 308. In some embodiments, the support 306 may incorporate the detector 106.

In operation, the lasers 304a-d may be directed toward the object 308. As in method step 204 of method 200, a first set of lasers 304a and 304b may measure a distance to a first surface 310 of the object 308 (e.g., the first obstruction). Similarly, a second set of lasers 304c and 304d may measure a distance to an obstruction. In the particular embodiment shown in FIG. 3, this obstruction would be support 306. In embodiments not employing support 306, lasers 304c and 304d would measure a distance to a second surface of object 308 (e.g., the bottom of the patient).

Measurements from lasers 304a, 304b, 304c, and 304d may then be used by controller 102 to estimate the volume of object 308 as described above in method step 204. In this example, if lasers 304c-d measured to the bottom surface 312 of support 306 (which is of a known thickness T), the thickness T of the support 306 could be incorporated to determine the actual distance to the object 308. In conjunction with the measurements of lasers 304a-b, the controller 102 may utilize this information to estimate a volume and select an X-Ray strength as in step 206.

Other arrangements, locations, and numbers of lasers 304 may be used to provide input to controller 102. For example, though shown in FIG. 3 as being directed to the same respective points, lasers 304a-b and lasers 304c-d may each be separately directed to four different points on the surface of object 308. In this way, four measurements may be taken simultaneously to be used in volume determination. Of course, should any other number of lasers 304 be used, any number of distances to object 306 could be measured.

Figure 4:
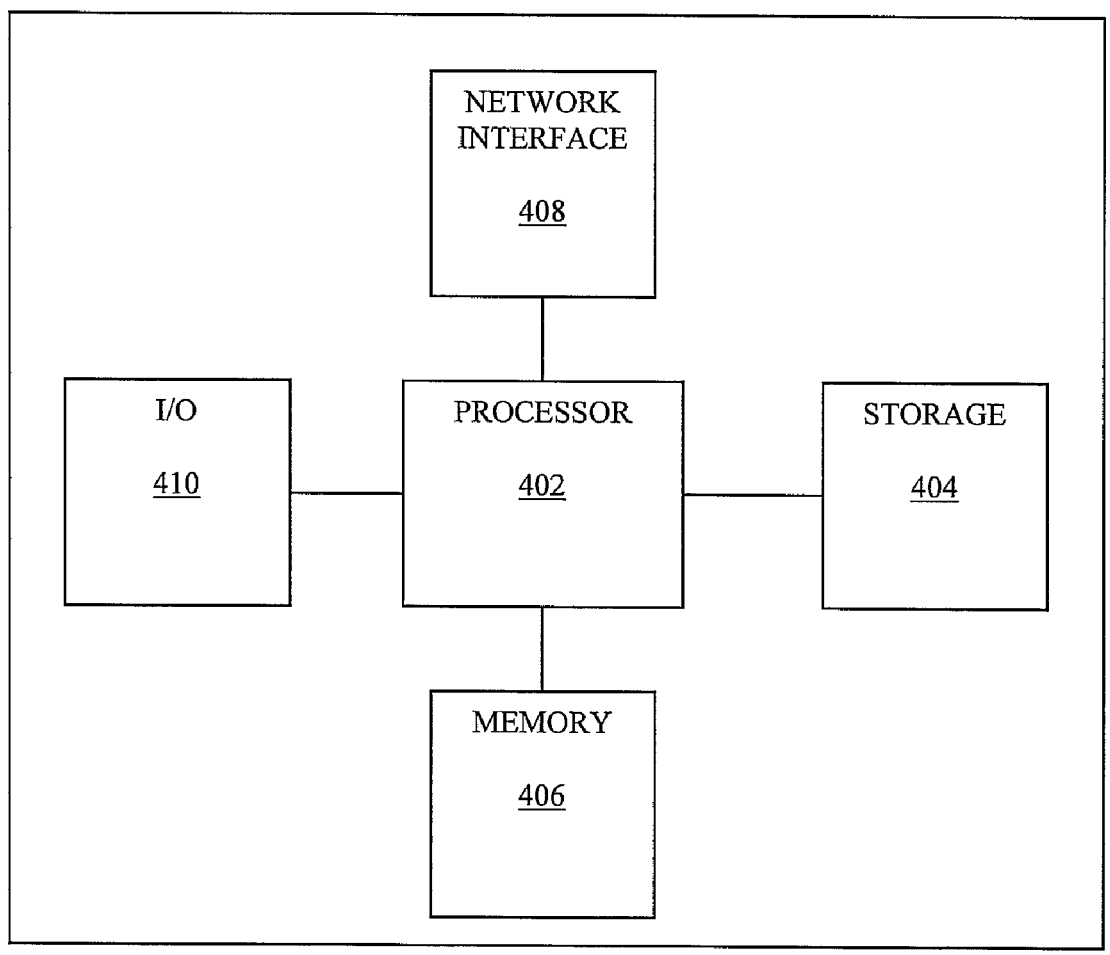
FIG. 4 is a detailed schematic drawing of a controller according to an embodiment of the invention.

FIG. 4 is a detailed schematic drawing of the controller 102 of FIG. 1. Controller 102 contains a processor 402 which controls the overall operation of the controller 102 by executing computer program instructions which define such operation. The computer program instructions may be stored in a storage device 404 (e.g., magnetic disk, database, etc.) and loaded into memory 406 when execution of the computer program instructions is desired. Thus, applications for performing the herein-described method steps, such as distance determination, volume estimation, and/or X-Ray strength determination and/or setting, be defined by the computer program instructions stored in the memory 406 and/or storage 404 and controlled by the processor 402 executing the computer program instructions. The controller 102 also includes one or more network interfaces 408 for communicating with other devices via a network. The controller 102 also includes other input/output devices 410 (e.g., display, keyboard, mouse, speakers, buttons, etc.) that enable user interaction with the controller 102. One skilled in the art will recognize that an implementation of an actual controller could contain other components as well, and that the controller of FIGS. 1 and 4 is a high level representation of some of the components of such a controller for illustrative purposes.

Further, the controller 102, X-Ray emitter 104, X-Ray detector 106, and/or range finding devices 108 may be implemented on, may be coupled to, and/or may include any components or devices that are typically used by, or used in connection with, a computer or computer system. Controller 102 and/or processor 402 may include one or more central processing units, read only memory (ROM) devices and/or random access memory (RAM) devices.

According to some embodiments of the present invention, instructions of a program (e.g., controller software) may be read into memory 406, such as from a ROM device to a RAM device or from a LAN adapter to a RAM device. Execution of sequences of the instructions in the program may cause the controller 102, X-Ray emitter 104, X-Ray detector 106, and/or range finding devices 108 to perform one or more of the method steps described herein. In alternative embodiments, hard-wired circuitry or integrated circuits may be used in place of, or in combination with, software instructions for implementation of the processes of an embodiment of the present invention. Thus, embodiments of the present invention are not limited to any specific combination of hardware, firmware, and/or software. The memory 406 may store the software for the controller 102, which may be adapted to execute the software program and thereby operate in accordance with the present invention and particularly in accordance with the methods described in detail below. However, it would be understood by one of ordinary skill in the art that aspects of the invention as described herein could be implemented in many different ways using a wide range of programming techniques as well as general purpose hardware sub-systems or dedicated controllers.

Such programs may be stored in a compressed, uncompiled and/or encrypted format. The programs furthermore may include program elements that may be generally useful, such as an operating system, a database management system and device drivers for allowing the controller to interface with computer peripheral devices, and other equipment/components. Appropriate general purpose program elements are known to those skilled in the art, and need not be described in detail herein.

The foregoing description discloses only particular embodiments of the invention; modifications of the above disclosed methods and apparatus which fall within the scope of the invention will be readily apparent to those of ordinary skill in the art. For instance, it will be understood that, though discussed primarily as an estimated volume, any other measurement parameters may be estimated such as weight, mass, density, thickness, etc. Similarly, other components may perform the functions of method 200 even when not explicitly discussed.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. A method for automatically setting X-Ray strength comprising:

automatically using at least one first range finding device mounted on a movable arm and being able to be directed to an object comprising a portion of patient anatomy to be X-rayed to determine a distance to said object to be X-rayed;

automatically estimating a volume of said object to be X-Rayed in response to the determined distance to said object to be X-rayed; and automatically selecting an X-Ray radiation strength based on the estimated volume for use in updating X-ray device settings to provide X-ray radiation of the selected strength to said object to be X-rayed.

2. The method of claim 1 wherein automatically estimating a volume of an object to be X-Rayed comprises:

automatically using a second range finding device and being able to be directed to an object to determine a distance to an object;

using the first and second range finding devices in determining a plurality of distances to one or more objects; and estimating the volume of said object to be X-Rayed based on the determined plurality of distances.

3. The method of claim 2 wherein:

said first and second range finding devices determine said plurality of distances to one or more objects using a plurality of collimated light beams;

a first of the plurality of distances comprises a distance to a portion of a body;

a second of the plurality of distances is the distance to a table for supporting the body; and the portion of the body is said object to be X-Rayed.

4. The method of claim 2 wherein the one or more of the objects includes the object to be X-Rayed.

5. The method of claim 1 wherein estimating the volume of an object to be X-Rayed comprises:
estimating the volume of the object to be X-Rayed within a plurality of predetermined ranges.

6. The method of claim 5 wherein the selected X-Ray strength corresponds to the one of the plurality of ranges.

7. The method of claim 1 wherein selecting the X-Ray strength comprises:
selecting an X-Ray wavelength, an X-Ray frequency, an X-Ray beam energy, or an X-Ray power.

8. The method of claim 2 further comprising:
estimating a density of the object to be X-Rayed based at least in part on the plurality of distances.

9. The method of claim 1 further comprising:
setting an X-Ray machine to transmit X-Rays at the selected strength.

10. A system for use in automatically setting X-Ray strength comprising:
at least one movable arm able to be directed to one or more objects including an object to be X-rayed;
a plurality of range finding lasers mounted on said at least one movable arm and configured to measure distances to said one or more objects including said object to be X-rayed to determine a distance to said object to be X-rayed; and
a controller configured to automatically estimate a volume of said object to be X-Rayed based on the measured distances and to automatically set an X-Ray strength based on the estimated volume for use in updating X-ray device settings to provide X-ray radiation of the selected strength to said object to be X-rayed.

11. A system for use in automatically setting X-Ray strength comprising:
a plurality of lasers configured to measure distances to one or more objects; and
a controller configured to automatically estimate a volume of one of the one or more objects based on the measured distances and to automatically set an X-Ray strength based on the estimated volume;
a support arm; and
wherein the plurality of lasers comprises:
a first plurality of lasers proximal to a first end of the support arm directed toward at least one of the objects; and
a second plurality of lasers proximal to a second end of the support arm directed toward at least one of the objects.

12. The system of claim 11 further comprising:
a table configured to support at least one of the objects, wherein the supported object is an object to be X-Rayed.

13. The system of claim 11 wherein the support arm is a c-arm.

14. An apparatus for automatically setting X-Ray strength comprising:
at least one movable arm able to be directed to one or more objects including an object to be X-rayed;
at least one range finding device mounted on said at least one movable arm and configured to measure distances to said one or more objects including said object to be X-rayed to determine a distance to said object to be X-rayed;
means for automatically estimating a volume of said object to be X-Rayed based on the measured distances; and
means for automatically selecting an X-Ray strength based on the estimated volume for use in updating X-ray device settings to provide X-ray radiation of the selected strength to said object to be X-rayed.

15. The apparatus of claim 14 wherein the means for automatically estimating a volume of an object to be X-Rayed comprises:
means for determining a first distance to one or more objects;
means for determining a second distance to one or more objects; and
means for estimating a volume of the object to be X-Rayed based on the determined first and second distances.

16. The apparatus of claim 15 wherein:
the first distance is the distance to a portion of a body;
the second distance is the distance to a table for supporting the body; and
the portion of the body is the object to be X-Rayed.

17. The apparatus of claim 14 wherein the means for estimating the volume of an object further comprises:
means for estimating the volume of the object within a plurality of predetermined ranges.

18. The apparatus of claims 17 further comprising:
means for corresponding the selected strength of the X-Ray to one of the plurality of ranges.

19. The apparatus of claim 14 further comprising:
means for automatically selecting at least one X-Ray parameter based on the estimated volume.

20. The apparatus of claim 15 further comprising:
means for estimating a density of the object to be X-Rayed based at least in part on the first and second distances.

21. The apparatus of claim 14 further comprising:
means for setting an X-Ray machine to transmit X-Rays at the selected strength.

* * * * *